(12) United States Patent
Tiemann et al.

(10) Patent No.: US 12,186,091 B2
(45) Date of Patent: Jan. 7, 2025

(54) BABY BOTTLE DEVICE

(71) Applicant: KONINKLIJKE PHILIPS N.V., Eindhoven (NL)

(72) Inventors: Christian Andreas Tiemann, Eindhoven (NL); Cornelis Bernardus Aloysius Wouters, Echt (NL); Lucja Elzbieta Bartula, Oirschot (NL); Lena Jaschke, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 762 days.

(21) Appl. No.: 17/277,990

(22) PCT Filed: Oct. 11, 2019

(86) PCT No.: PCT/EP2019/077623
§ 371 (c)(1),
(2) Date: Mar. 19, 2021

(87) PCT Pub. No.: WO2020/074716
PCT Pub. Date: Apr. 16, 2020

(65) Prior Publication Data
US 2021/0369184 A1 Dec. 2, 2021

(30) Foreign Application Priority Data
Oct. 11, 2018 (EP) ..................... 18199799

(51) Int. Cl.
*A61B 5/00* (2006.01)
*A61B 5/113* (2006.01)
*A61J 9/00* (2006.01)

(52) U.S. Cl.
CPC ............ *A61B 5/4205* (2013.01); *A61B 5/113* (2013.01); *A61J 9/00* (2013.01); *A61B 2503/04* (2013.01);
(Continued)

(58) Field of Classification Search
CPC ..... A61B 5/113; A61B 5/1118; A61B 5/4205; A61B 5/4866; A61B 2503/04;
(Continued)

(56) References Cited

U.S. PATENT DOCUMENTS

| 9,974,476 B2 | 5/2018 | Aron et al. | |
| 2015/0208979 A1* | 7/2015 | Cunningham | A61B 5/228 |
| | | | 600/590 |
| 2016/0354286 A1 | 12/2016 | Lepine | |

FOREIGN PATENT DOCUMENTS

| CN | 104997642 | 10/2015 |
| CN | 205163676 U * | 4/2016 |

(Continued)

OTHER PUBLICATIONS

Wang, et al. "Development of a Wireless Oral-Feeding Monitoring System for Preterm Infants", IEEE Journal of Biomedical and Health Informatics, vol. 19, No. 3, May 1, 2015 (Year: 2015).*
English translation of CN-106205070-A (Year: 2016).*
English translation of CN-205163676-U (Year: 2016).*
International Search Report and Written Opinion dated Nov. 7, 2019 for International Application No. PCT/EP2019/077623 filed Oct. 11, 2019.

(Continued)

*Primary Examiner* — Christine H Matthews
*Assistant Examiner* — Anna Roberts (57) ABSTRACT

A baby bottle device (100) is provided which comprises at least one 100 movement sensor (140, 150) for detecting a movement of the baby bottle device (100). The movement data from the movement sensor (140, 150) is analyzed in an analyzer (200) to perform a suck-swallow-breathe analysis during a drinking phase of the baby based on the movement data from the movement sensor (140, 150). Thus, a drinking behavior of a baby can be efficiently analyzed.

14 Claims, 11 Drawing Sheets

(52) U.S. Cl.
CPC ............. *A61B 2560/0462* (2013.01); *A61B 2562/0219* (2013.01); *A61J 2200/70* (2013.01)

(58) Field of Classification Search
CPC ..... A61B 2560/0462; A61B 2562/0219; A61J 9/00; A61J 2200/70; G16H 20/60; G16H 40/63
See application file for complete search history.

(56) References Cited

FOREIGN PATENT DOCUMENTS

| CN | 106205070 A | * | 12/2016 | ............. | G08B 21/24 |
|---|---|---|---|---|---|
| WO | 2013061242 | | 5/2013 | | |
| WO | 2018/053045 | | 3/2018 | | |

OTHER PUBLICATIONS

Wang, et al: "Development of a Wireless Oral-Feeding Monitoring System for Preterm Infants", IEEE Journal of Biomedical and Health Informatics, vol. 19, No. 3, May 1, 2015.
De Vries, et al: "The emergence of fetal behavior: I. Qualitative aspects.", Early Human Development, 7(4), 301-322, 1982.
Bu'lock, et al: "Development of coordination of sucking, swallowing and breathing: Ultrasound study of term and preterm infants", Developmental Medicine and Child Neurology 32(8): 669-678, 1990.
Riordan J., Wambach K., Breastfeeding and human lactation, 4th edition (2010); Sudbury, MA: Jones and Bartlett.

* cited by examiner

BABY BOTTLE DEVICE

CROSS REFERENCE TO RELATED APPLICATIONS

This application is the U.S. National Phase application under 35 U.S.C. § 371 of International Application No. PCT/EP2019/077623 filed Oct. 11, 2019, which claims the benefit of European Patent Application Number 18199799.0 filed Oct. 11, 2018. These applications are hereby incorporated by reference herein.

FIELD OF THE INVENTION

The present invention relates to a baby bottle device, a method of analyzing a drinking behavior of a baby and a baby bottle movement analyzer.

BACKGROUND OF THE INVENTION

A baby which is drinking from a breast of its mother or from a bottle needs to master a complex process of precise coordination of sucking, swallowing and breathing. From approximately 32 to 34 weeks of gestational age on, a baby is typically able to perform the suck-swallow-breathe pattern.

Figure 1:
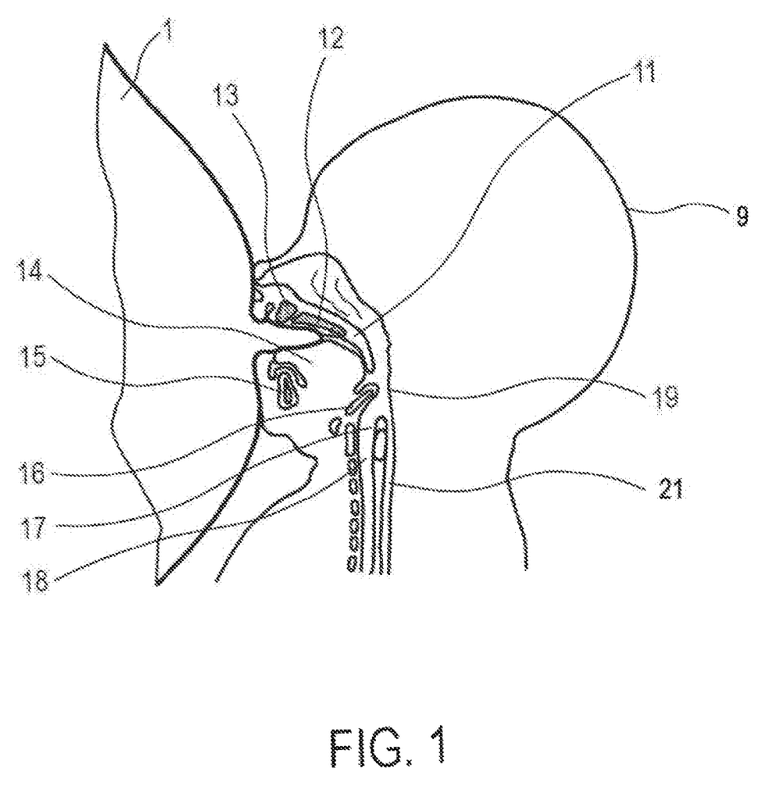
FIG. 1 shows a schematic representation of a breast feeding baby.

FIG. 1 shows a schematic representation of a breast feeding baby. In FIG. 1, the baby 9 as well as a breast 1 of the mother are depicted. Furthermore, the intraoral space of the baby having a soft palate 11, a hard palate 12, an alveolar ridge 13, a tongue 14, a mandible 15, an epiglottis 16, larynx 17, trachea 18, a pharyngeal wall 19 and an esophagus 21 is present. These sucking and swallowing begins with the compression of the breast nipple or a bottle's teat. This is accompanied by a creation of an intraoral pressure and lowering the jaw in order to extract milk into the pharynx. As the tube or pharynx is used for the digestive system as well as the respiratory system, it must be reconfigured such that the baby can eat and breathe at the same time. The elevation of the palate 11 and the closure of the larynx 17 occur as pharyngeal muscle contraction and relaxation moving the amount of milk further into the esophagus 21 into a stomach of a user.

Wang Yu-Lin et al.: "Development of a Wireless Oral-Feeding Monitoring System for Preterm Infants", IEEE Journal of Biomedical and Health Informatics, IEEE, Piscataway, N.J., USA, Vol. 19, no. 3, 1 May 2015, pages 866-873, discloses a baby bottle device with a sensor to detect a suck-swallow-breathe complex of an infant. A pressure sensor, a microphone and electrodes for EMG measurements are used.

US 2016/354286 A1 discloses a baby bottle with a motion sensor which is used to monitor a milk flow.

CN 104997642 A discloses a baby bottle with a bottle sleeve which includes sensors to detect a movement of the bottle during the feeding of a baby. The sensor comprises a temperature sensor to detect the temperature of the milk. Based on the movement data from the sensor a milk drinking plan can be provided.

It is known that the sucking reflex has a non-nutritive mode and a nutritive mode. The non-nutritive suck NNS is an early developed motor reflex, wherein no nutrition are obtained. The non-nutritive suck NNS is performed in bursts of suck and pause periods to accommodate the respiration. The typical non-nutritive suck pattern consists of 6 to 12 suck cycles per burst including an intra-burst frequency of two suck cycles per second (2 Hz). On the other hand, nutritive sucking NS is slower and occurs during the feeding of the baby, in particular when milk is transferred at a rate of 1 suck per second as an undisturbed sequence of sucking-swallowing-breathing. In view of the complex sucking-swallowing-breathing pattern, it is desirable to obtain more detailed insights in the drinking behavior.

SUMMARY OF THE INVENTION

It is an object of the invention to provide a baby bottle device which allows an unobtrusive analyzing of the drinking behavior of the baby.

According to an aspect of the invention, a baby bottle device is provided which comprises at least one movement sensor for detecting a movement of the baby bottle device. The movement data from the movement sensor is analyzed in an analyzer to perform a suck-swallow-breathe analysis during a drinking phase of the baby based on the movement data from the movement sensor.

According to an embodiment, the movement sensor comprises an accelerometer and a gyroscope which may be a single or multiple axis sensor. Thus, linear and rotational accelerations of the bottle and movements of the bottle are detected.

According to an embodiment, a housing e.g. in form of a sleeve is provided which can be removeably attached to the baby bottle, for example to the milk container. This is advantageous as the housing (sleeve) which may include the movement sensor and/or the movement analyzer will not be in contact with the fluid in the container. Moreover, as the sleeve is removable it can be used with several baby bottles or different containers. Therefore, the housing (sleeve) does not need to be cleaned as intensively as a milk container. Based on the movement measurements of the bottle as a whole drinking pattern of a baby can be determined.

According to an embodiment, the baby bottle device comprises a transmitter for transmitting the movement data from the movement sensor or the analyzed suck-swallow-breathe behavior from the movement analyzer. The movement data or the drinking behavior of the baby can thus be analyzed by an external device. Optionally, such an external device may output an indication of the movement data or the drinking behavior to the parent or doctor.

According to an embodiment, the movement sensor comprises at least one single or multiple axis accelerometer and at least one single or multiple axis gyroscope.

According to an embodiment, the movement analyzer determines drinking parameters or behavior of the baby. The drinking parameters include at least one of a burst duration, a pause duration, a burst-pause duration ratio, a number of sucks per burst, a sucking frequency, a sucking magnitude and drinking interruptions. Thus, the drinking behavior can be analyzed in detail.

According to a further embodiment, the baby bottle device comprises a teat. The post processor can be configured to analyze current drinking parameters to monitor a performance of the teat. Thus, by means of the baby bottle device, it can be determined whether the current teat is the right one for the baby. Based on the performance of the teat, it can be determined whether the holes of the teat are too large or too small. Thus, the baby bottle device according to the invention may be used for a teat replacement service.

According to a further embodiment, a baby bottle movement analyzer is provided which can determine between a drinking period and a non-drinking period based on the movement data of the movement sensor. With such a movement analyzer, it is possible to analyze the non-drinking period in greater detail.

According to a further embodiment, the baby bottle device comprises a housing e.g. in form of a sleeve, which can be attached to the baby bottle device. The movement analyzer can be arranged in the housing.

According to a further embodiment, the movement analyzer outputs the current drinking parameters in real time such that an immediate feedback can be given to the parent. For real time analysis, a threshold used to determine whether or not the drinking parameters are acceptable can be implemented as a variable threshold.

According to an embodiment, a non-obtrusive way of analyzing suck-swallow-breathe behavior of a baby is provided. Furthermore, a non-obtrusive way to detect burst-pause cycles of a baby based on movement data from the baby bottle device is provided. With this information, parents and clinicians can be provided with detailed information on the drinking behavior of the baby.

According to a further aspect of the invention, a method of analyzing a drinking behavior of a baby using a baby bottle device is provided. The baby bottle device comprises optionally a fluid controller and at least one movement sensor coupled to the baby bottle device. A suck-swallow-breathe behavior is analyzed based on a movement of the baby bottle device as detected by at least one movement sensor coupled to the baby bottle.

According to an embodiment, the at least one movement sensor comprises at least one single or multiple axis accelerometer and at least one single or multiple axis gyroscope.

According to a further embodiment, drinking parameters like burst duration, a pause duration, a burst-pause duration ratio, a number of sets per burst, a sucking frequency, a sucking magnitude and/or drinking interruptions are determined.

According to an embodiment, the movement sensor can be optionally attached or arranged at an adapter between the fluid container and a teat.

According to a further aspect of the invention, a computer program for operating a baby bottle device is provided. The computer program comprises program code means for causing the baby bottle device to carry out the steps of analyzing a drinking behavior of a baby, when the computer program is run on a computer or device controlling the baby bottle device.

Other aspects of the invention are described in the dependent claims. Further advantages and embodiments of the invention will now be elucidated with reference to the drawings.

It shall be understood that a preferred embodiment of the present invention can also be any combination of the dependent claims or above embodiments with the respective independent claim.

These and other embodiments of the invention will be apparent from and elucidated with reference to the embodiments described hereinafter.

DETAILED DESCRIPTION OF EMBODIMENTS

Figure 2:
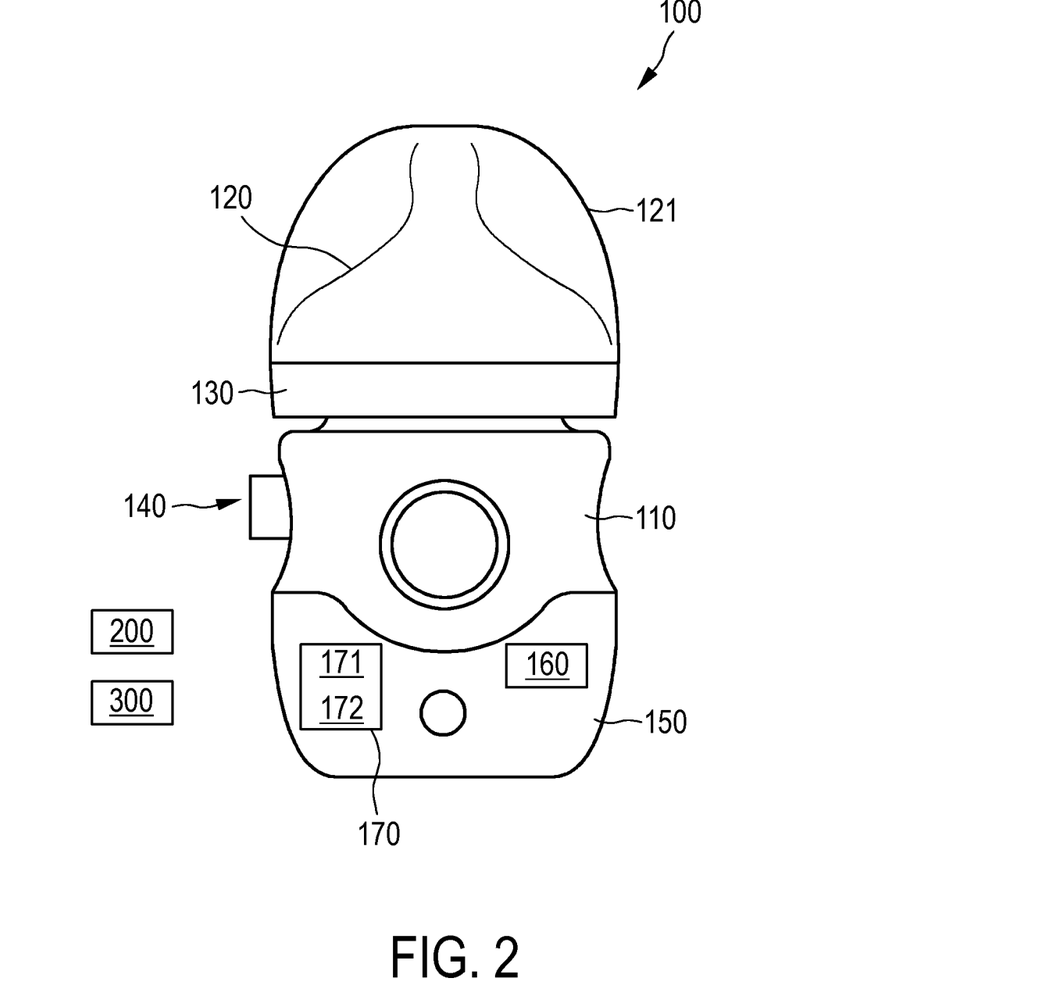
FIG. 2 shows a block diagram of a baby bottle device according to an embodiment of the invention.

FIG. 2 shows a block diagram of a baby bottle device according to an embodiment of the invention. The baby bottle device 100 comprises a milk bottle or fluid container 110, a teat 120, optionally a cap 121, an adapter 130 arranged between the bottle 110 and the teat 120, a first movement sensor 140 or a second movement sensor 150. Optionally a movement analyzer 200 is provided as part of the baby bottle device to analyze the movement data. The movement analyzer 200 can also be provided in or at an external device.

A housing 151 (e.g. in form of a sleeve) can be attached to the baby bottle, e.g. to the fluid container or to the adapter 130.

The movement sensor 140/150 is used to detect the movements of the bottle in particular during the feeding of a baby. The data of the movement sensor 140/150 can be used by the movement analyzer 200 to detect whether the baby is drinking or not (for example, in order to prevent excessive air intake). Furthermore, the movement data can be used to detect whether or not the teat being used is the correct one (e.g. by analyzed the flow rate to determine whether it is too high or too low). Moreover, based on the movement data, it can be detected during a feed whether the baby is satisfied or is getting tired. Alternatively, based on the movement data it can be detected if the baby is gulping for example at the start of the feed, typically as it is very hungry. Furthermore, the movement data can be analyzed also over time to obtain objective information on the sucking-swallowing-breathing behavior of the baby.

The movement sensor 140/150 can be removably attached to baby bottle device or can be integrated into the baby bottle device. Preferably, the movement sensor 140/150 is removably attached to the baby bottle such that it can be used with different bottles, for example if one bottle needs to be cleaned.

The housing 151 can comprise the movement sensor and can for example be implemented as a sleeve which can be attached to the bottom or a side of the milk container 110. Alternatively, the sensor 140 can be attached to the bottle with an elastic strap. The sensor 140, 150 may also be integrated with or attached to the adapter 130.

According to an embodiment of the invention, the movement data from the movement sensor 140, 150 can be further analyzed in a mobile device, a backend-server or a cloud-based system. Accordingly, the baby bottle device 100 can optionally comprise a transmitter 160 for transmitting the detected and/or analyzed movement data. The transmitter 160 can be transmitting via Wi-Fi, Bluetooth™, 4G, 5G, etc. It can be arranged in or attached to the bottle 110, the adapter 130 or the sensor 140 or 150. Preferably, the transmitter 160 is arranged in or at the housing 151.

The movement sensor 140, 150 may detect the motion and an angle of the bottle 110 during the feeding. The sensor 140, 150 may comprise an inertial measurement unit IMU 170 which may comprise a single or multiple axis accelerometer 171 and/or a single or multiple axis gyroscope 172. Alternatively, one accelerometer 171 may be used in order to obtain the movement data. The inertial measurement unit 170 can be arranged in or at the housing 151.

According to an aspect of the invention, the data from the inertial measurement unit 170 during the feed can be analyzed by the movement analyzer 200 to detect whether such data can be used for a suck-swallow-breathe SSB analysis. Based on these data, parameters related to the suck-swallow-breathe rhythm can be determined by the analyzer 200. These parameters may include a burst duration, a pause duration, a burst-pause duration ratio, a number of sucks per burst, a sucking frequency, a sucking magnitude and/or drinking interruptions.

The determined suck-swallow-breathe parameters may be undergoing a post processing in a post-processer 300 for a more detailed analysis. This more detailed analysis may be used for the insight and guidance for parents and doctors regarding the drinking behavior of the baby. The detected or calculated parameters of the suck-swallow-breathe procedure may be compared with threshold values by the analyzer 200 or to determine whether the detected or measured parameters are within the acceptable range. Furthermore, the determined parameters of the suck-swallow-breathe may be analyzed post-processer 300 in view of trends within a feed or between feeds. Based on these parameters, it may be determined whether the baby is satisfied, has drunk enough, is tired, is gulping or an impropriate teat has been used.

The movement data could for instance be used in a teat replacement service. Here, parents can be informed on when to replace the teat, and receive advice by what kind of teat (e.g., to lower or increase the flow rate) should be used. The flow rate is not measured directly, but characteristics of the burst-pause cycle may indirectly indicate if the flow rate is too high or too low. For instance, the continuous presence of very long burst periods throughout feedings in young infants may indicate that the flow rate is too high. Optionally, a feedback (optical or audio feedback) can be given to the parents or doctors in order to improve the feeding efficiency of the baby.

Optionally, the housing 151 can comprise a movement sensor 150, the transmitter 160 and/or the inertial movement unit. Moreover, the movement analyzer 200 can be arranged in or at the housing 151.

Figure 3:
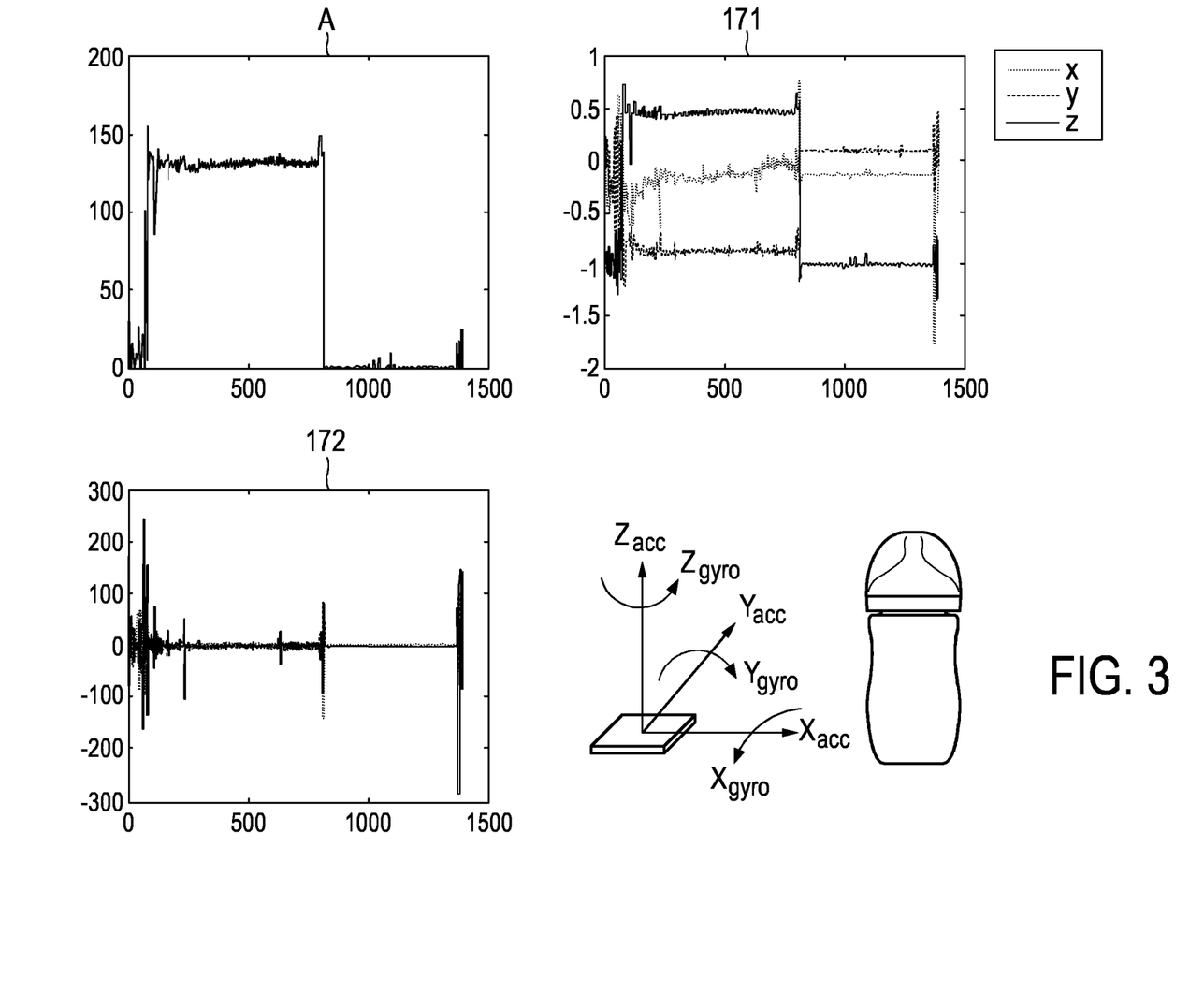
FIG. 3 shows various graphs depicting the detectable movements of a baby bottle.

FIG. 3 shows various graphs depicting the detectable movements of a baby bottle. With the movement sensor 140, 150, the movement of the bottle 110 in the x, y, z direction can be detected over time T. Furthermore, the rotation round the x axis, y axis and z axis can be detected, in particular by means of the gyroscope.

According to an embodiment of the invention, the movement sensor 140, 150 may be implemented as a sleeve 150 comprising an accelerometer 171 and a gyroscope 172. These two sensors 171, 172 may be operated at a sampling frequency which is sufficiently high to capture the sucking frequency which is around 1-2 Hz. For example, the sampling frequency can be between 10 and 50 Hz or higher.

In FIG. 3, the raw signals of the angle A, the accelerometer 171 and the gyroscope 172 are depicted. If the bottle 100 is vertically arranged, then the angle is 0° and if the bottle 100 is horizontally arranged, then the angle is 90°. Accordingly, based on the detected angle A of the bottle 100, the start and end of a feeding of the baby can be detected. Furthermore, interruptions of the feeding process may also be detected by analyzing the angle of the bottle.

Figure 4:
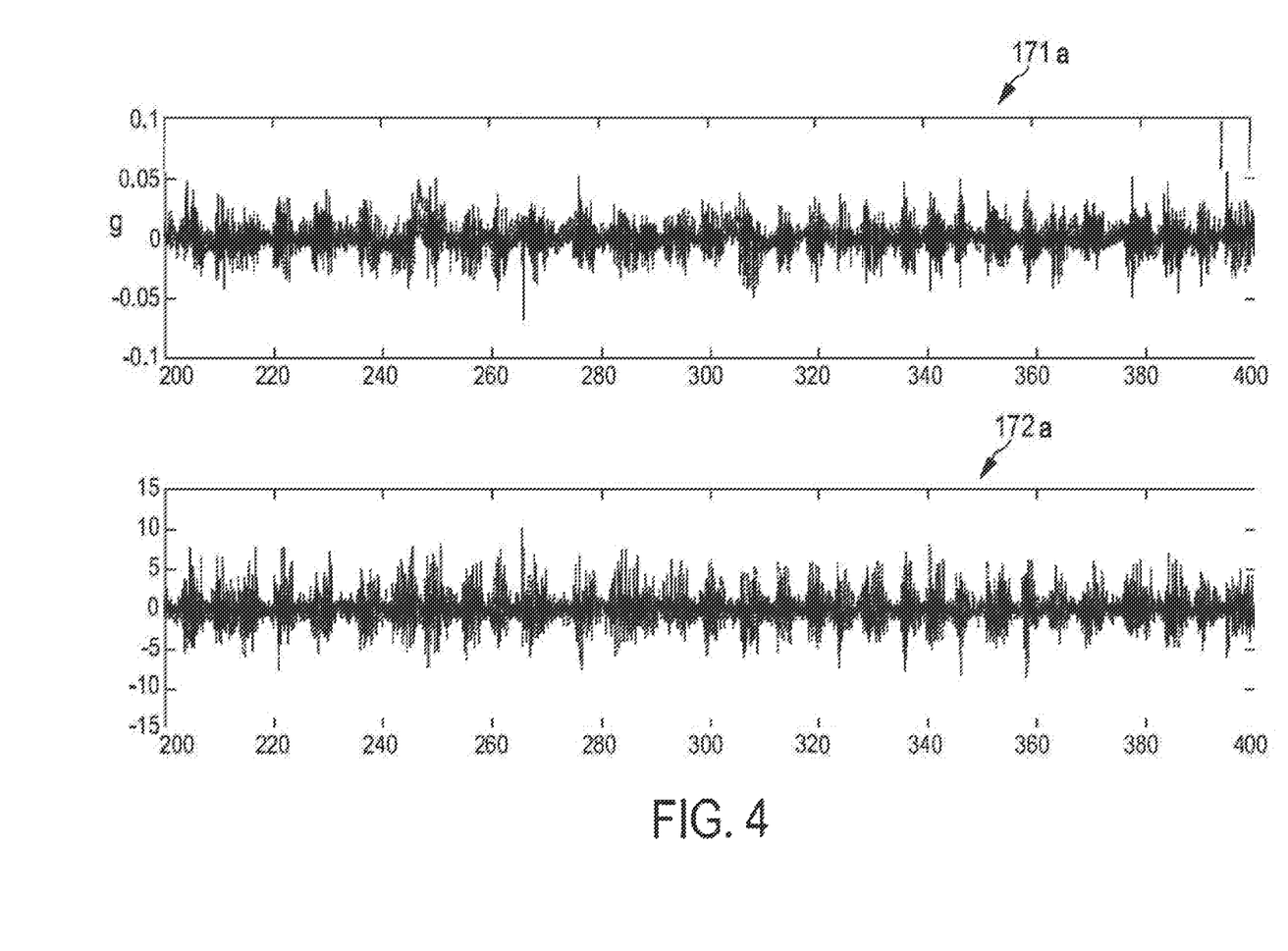
FIG. 4 shows a graph depicting accelerometer and gyroscope signals during the use of a baby bottle device according to an embodiment of the invention.

FIG. 4 shows a graph depicting accelerometer and gyroscope signals 171a, 172a during the use of a baby bottle device according to an embodiment of the invention. FIG. 4 depicts the accelerometer signals 171a and the gyroscope signals 172a of a bottle during use over an angle of the bottle. As can be seen, the signal has regular patterns. From the data of the accelerometer 171 and the gyroscope 172, it is clear that periods of increased motion and reduced motion alternate. These alternate motion periods relate to a burst/pause cycle with short periods of drinking and breaks in between. It should be noted that the suck-swallow-breathe motion occurs during the burst periods. High frequency fluctuations in the signals can relate to a sucking behavior of the baby.

Figure 5:
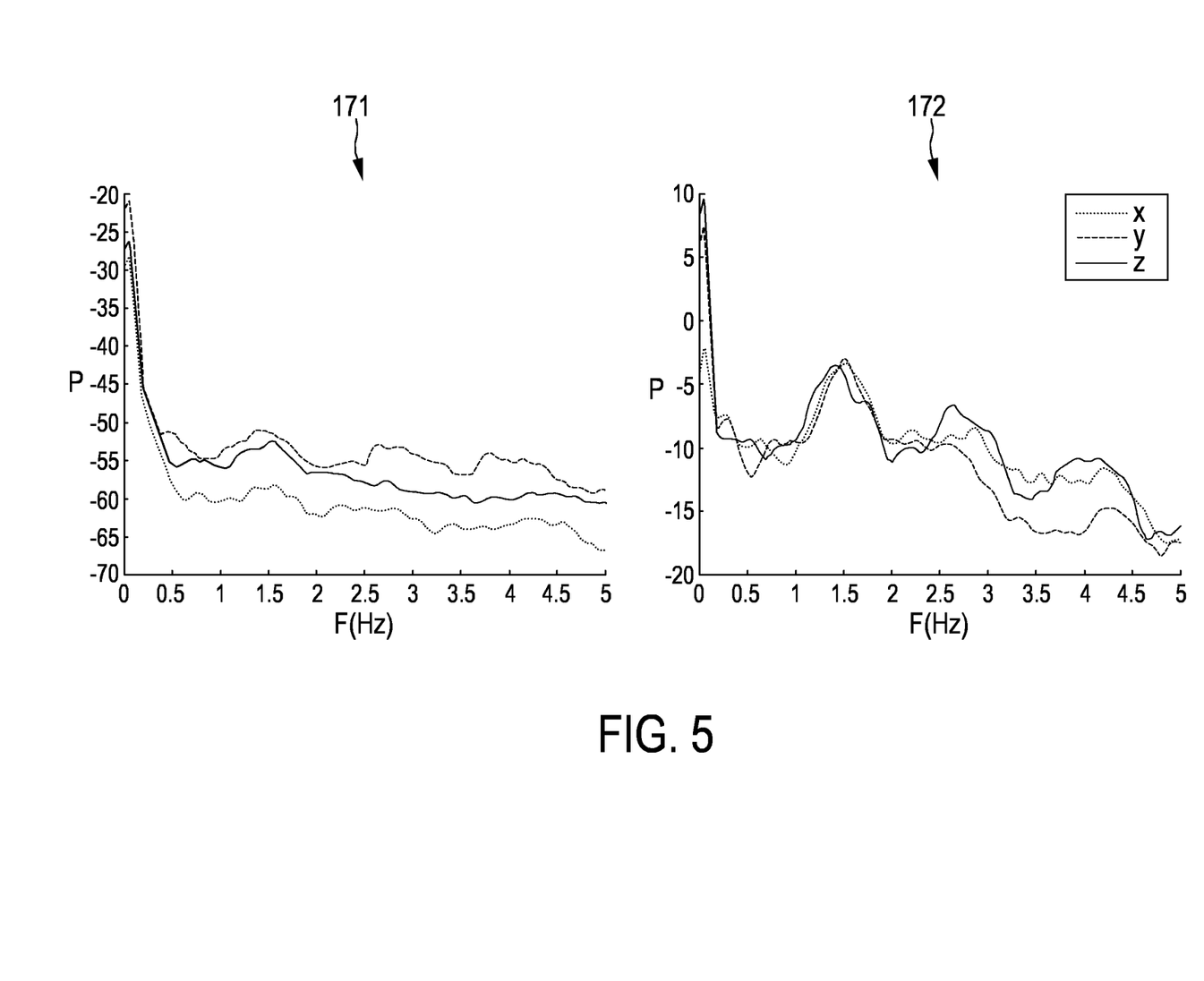
FIG. 5 shows a graph depicting a power spectral density of the accelerometer and gyroscope signals according to an embodiment of the invention.

FIG. 5 shows a graph depicting a power spectral density P of the accelerometer and gyroscope signals 171, 172 over frequency F(Hz) according to an embodiment of the invention. As can be seen in FIG. 5, two dominant frequency ranges between 0-0.5 Hz related to the burst-pause cycle and a frequency range between 1 and 2 Hz related to the sucking is present in the power spectral signal. From the analysis of the accelerometer signal and the gyroscope signal, it becomes clear that the sucking frequency is more pronounced in the gyroscope signal. Thus, the angular movements appear to be more pronounced than the linear movements during the sucking.

Figure 6:
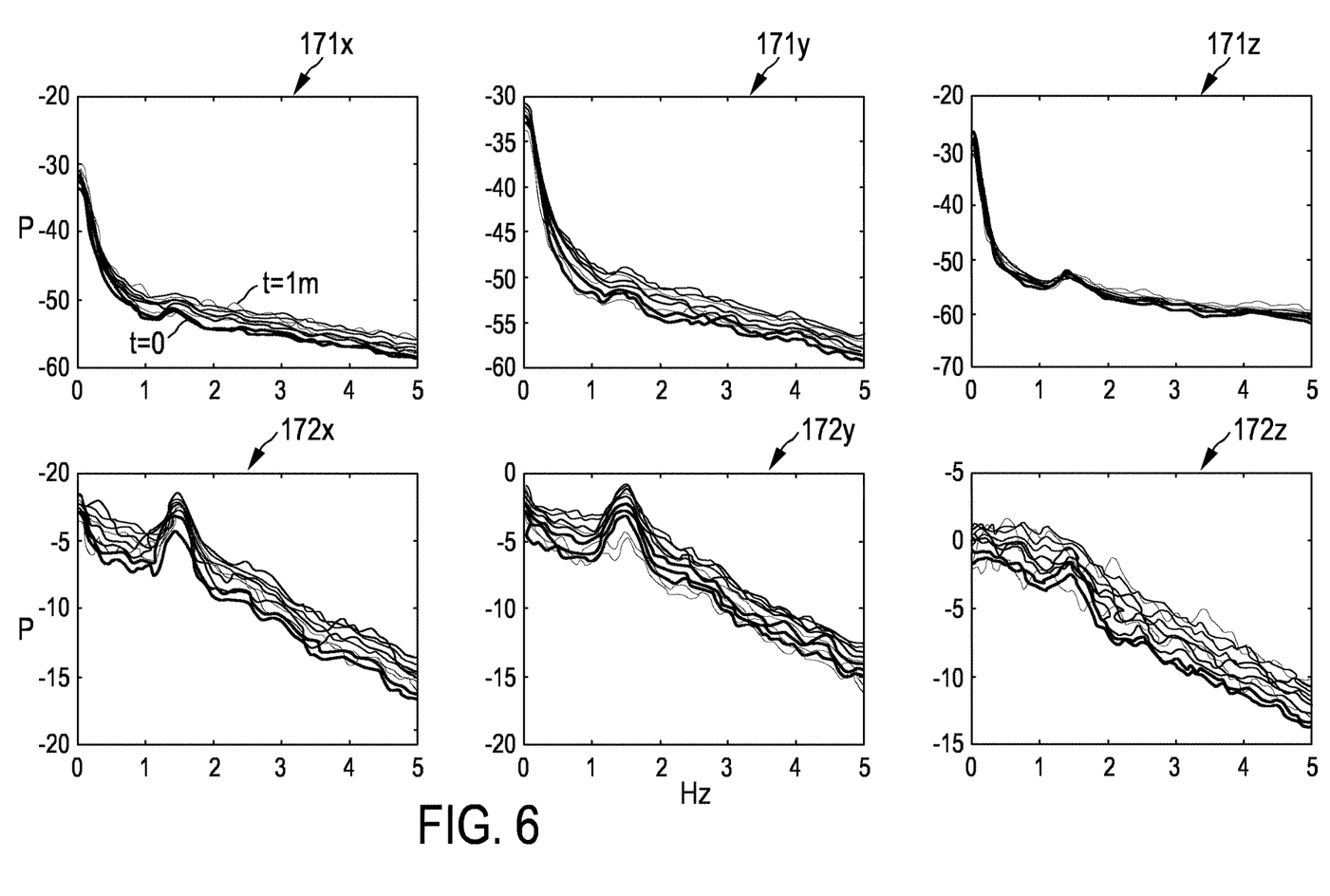
FIG. 6 shows different graphs depicting a moving average of spectral densities according to an embodiment of the invention.

FIG. 6 shows different graphs depicting a moving average of spectral densities P according to an embodiment of the invention. In FIG. 6, a moving average of spectral densities P of all these components $171x$, $171y$, $171z$ of the accelerometer 171 of all three components $172x$, $172y$, $172z$ gyroscope signal are depicted. As can be seen, the sucking frequency can be noticed in the z-component $171z$ of the accelerometer signal 171 corresponding to the linear motion along the longitudinal axis of the bottle during sucking. On the other hand, the magnitude of the signal is lower.

Figure 7:
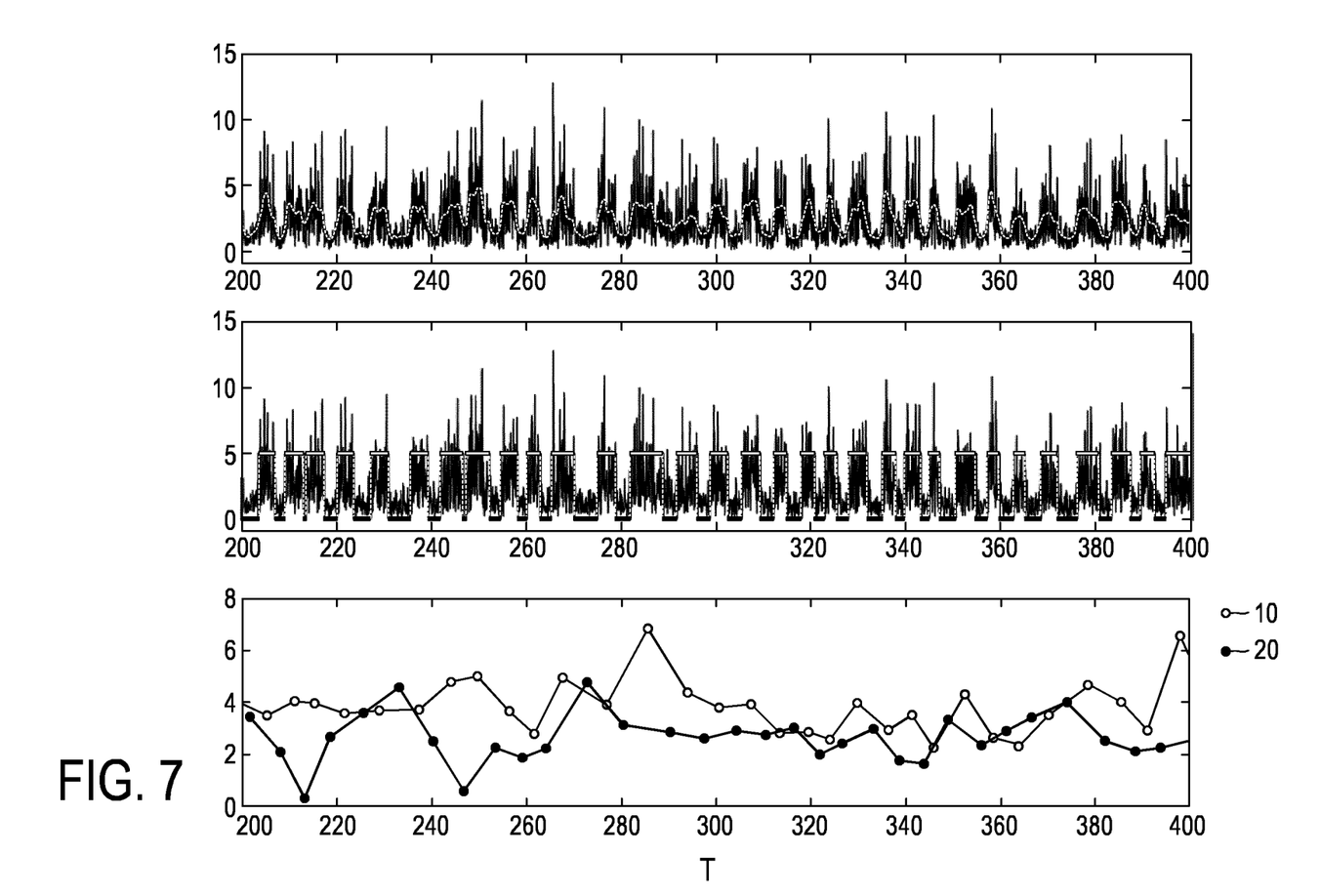
FIG. 7 shows a graph depicting a raw gyroscope magnitude, a low-pass filtered gyroscope magnitude, a gyroscope magnitude with burst-pause periods and durations of extracted burst and pause durations according to an embodiment of the invention.

FIG. 7 shows a graph depicting a raw gyroscope magnitude, a low-pass filtered gyroscope magnitude, a gyroscope magnitude with burst-pause periods and durations of extracted burst and pause durations according to an aspect of the invention. According to an embodiment of the invention, bursts and pauses can be extracted based on the magnitude of the gyroscope signal. In order to perform this analysis, a low-pass-filtering of the gyroscope magnitude as well as an application of a threshold can be performed. Alternatively, the bursts 10 and pauses 20 can be analyzed based on clustering. If the bursts 10 and pauses 20 have been analyzed, they can be used to calculate the duration thereof. The determined duration of the bursts 10 and pauses 20 can be further examined to determine whether they are in the expected range or whether certain trends can be observed.

Figure 8:
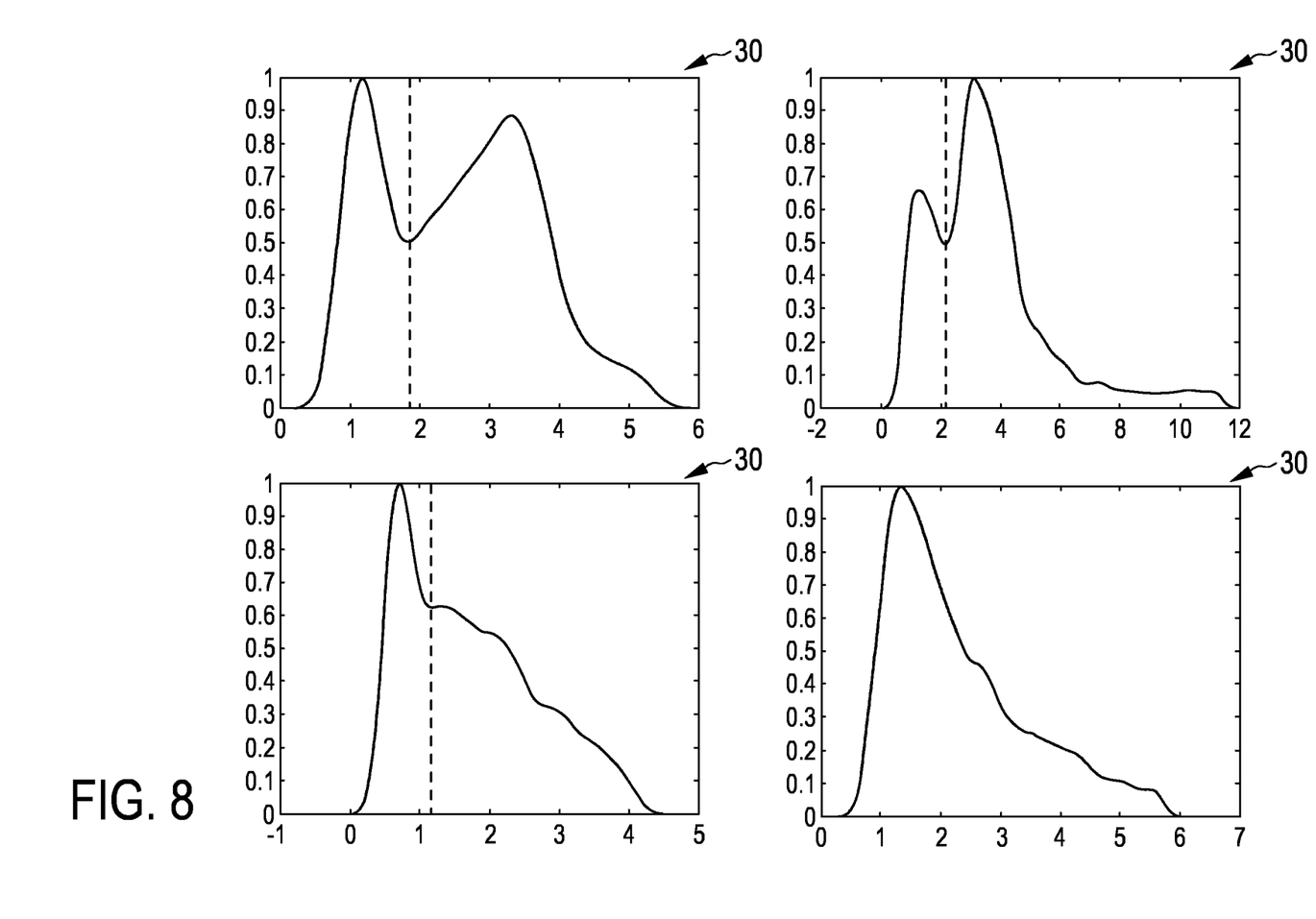
FIG. 8 shows a graph depicting histograms of low pass filtered gyroscope signals according to an embodiment of the invention.

FIG. 8 shows a graph depicting gyroscope histograms 30 of low pass filtered gyroscope signals according to an aspect of the invention. In FIG. 8, histograms 30 of feeds are depicted (the densities of the gyroscope signal is depicted over the gyroscope signal (deg/s)) where two modes are visible regarding two pauses 20 and bursts 10. According to an embodiment of the invention, a threshold is selected to separate bursts from pauses. A value and the minimal density between the peaks correspond to a preferred threshold to separate the burst from the pause modes. The two lower graphs in FIG. 8 depict certain samples, where it is not possible to discern between burst and pause modes.

The method based on a constant threshold requires that all movement data from a feed is collected, before histograms can be made. Only then a threshold to separate burst from pause can be determined. For some applications it is, however, useful to detect drinking in behavior real-time, such that immediate feedback can be given to parents. One method is to use exponential filtering/smoothing to real-time estimate a threshold and determine if the baby is drinking or not. For example, two exponential filters could be applied, one with a low forgetting factor to heavily smooth the accelerometer/gyroscope magnitude signal. This filter can be seen as smooth moving average which is being used as the threshold. The second exponential filter has a higher forgetting factor and smooths the data to remove the high frequencies and noise, but the burst-pause dynamics are preserved. This signal in combination with the variable threshold can be used to determine if the baby is drinking.

According to an aspect of the invention, these signals from the gyroscope and the accelerometer 171, 172 may be further analyzed e.g. by the analyzer regarding time series signals like a number of sucks, sucking frequency, a sucking strength and a regularity of suck-to-suck intervals. According to an embodiment of the invention, a post analysis or post-processing of the drinking parameters can be used to provide personalized insight for parents and doctors. The analysis of the gyroscope and accelerometer data can provide parents valuable information to understand the drinking behavior of the child. For example, the detected signals may be analyzed to determine whether the baby is satisfied and has drunk enough during the feeding. Alternatively, it can be determined whether the baby is tired, is gulping or if an inappropriate teat has been used.

Figure 9:
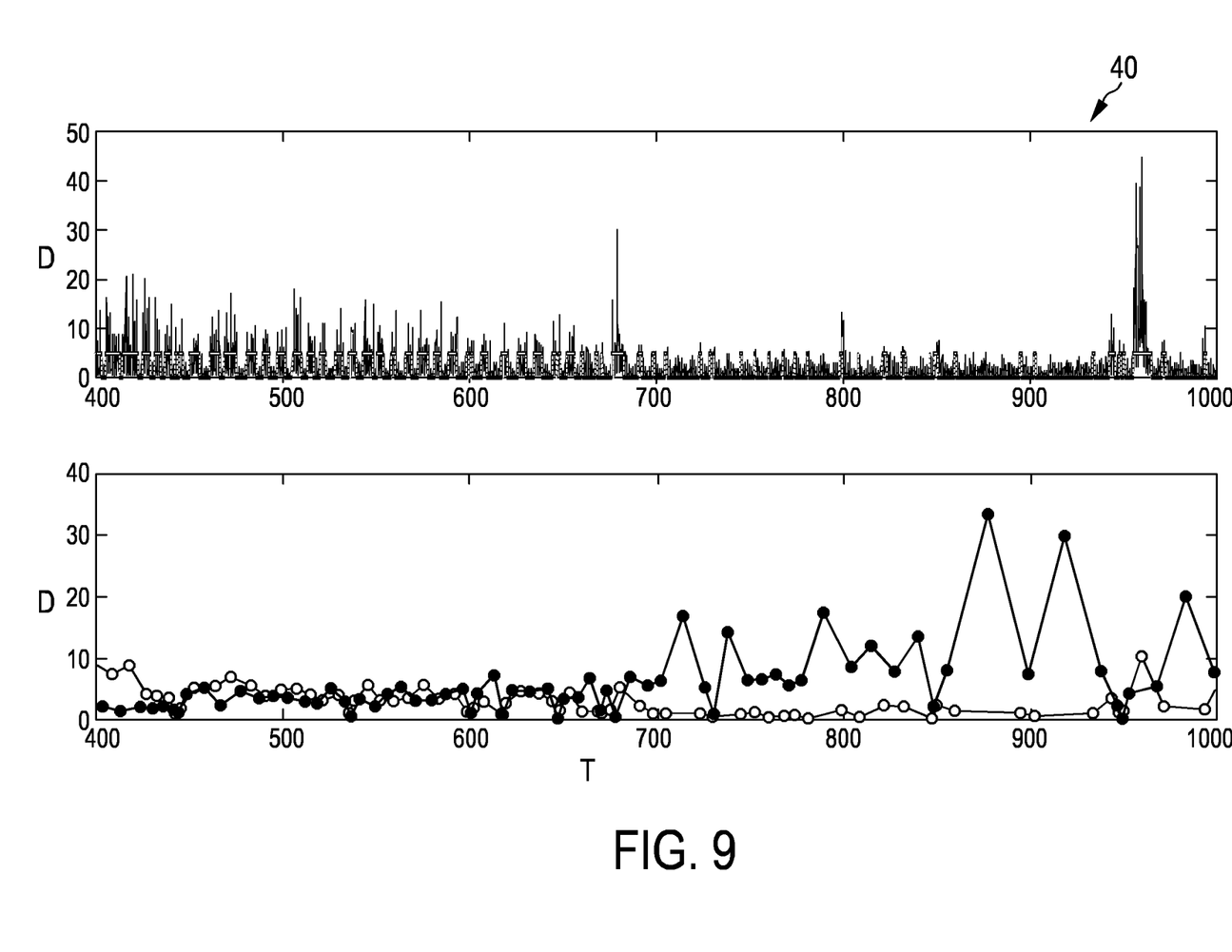
FIG. 9 shows a graph depicting a sample of a feed with a sudden increase in pauses according to an embodiment of the invention.

FIG. 9 shows a graph depicting a sample of a feed with a sudden increase in pauses according to an aspect of the invention. FIG. 9 shows the duration of bursts over time T (sec) of the gyroscope signals as well as the changes in magnitude 40 of the gyroscope signal over time T. As can be seen from FIG. 9, the duration D of the bursts and pauses is substantially stable during the first 700 seconds. After this point, the baby may start to take longer pauses and to drink at a slower rate. Accordingly, the baby may have drunk sufficient, is distracted or is tired. Optionally, this information may be outputted by the baby bottle device to the parents optionally via an external electronic device.

Figure 10:
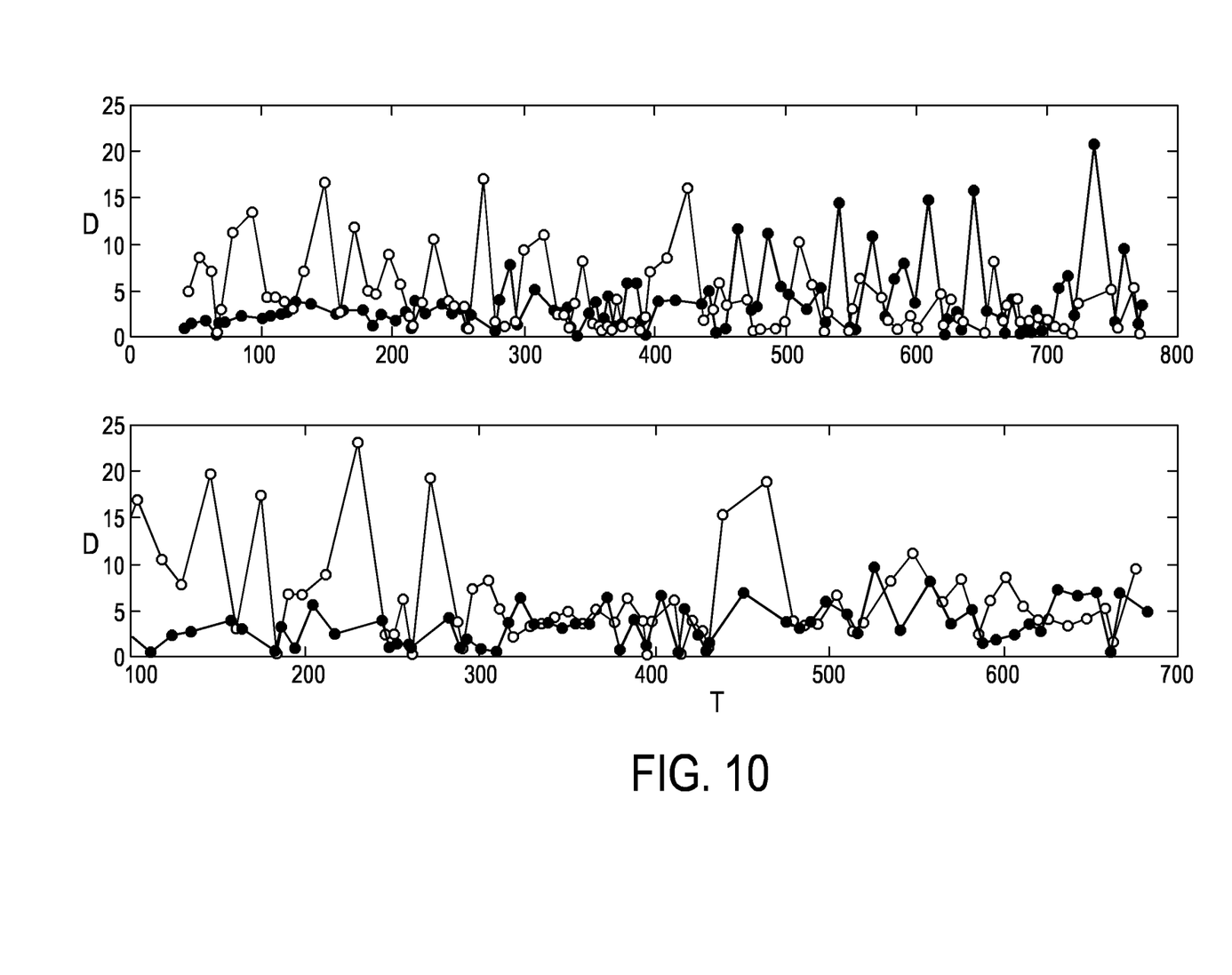
FIG. 10 shows a graph depicting examples of feeding of a baby according to an embodiment of the invention.

FIG. 10 shows a graph depicting examples of feeding of a baby according to an aspect of the invention. Here, two drinking periods and in particular the durations D of the burst are depicted over time T. From FIG. 10, it is clear that the baby starts with long drinking periods (for example because it is hungry). Thereafter, the drinking periods are getting shorter and the break periods are getting longer. Accordingly, the baby may be becoming tired and exhausted.

Figure 11:
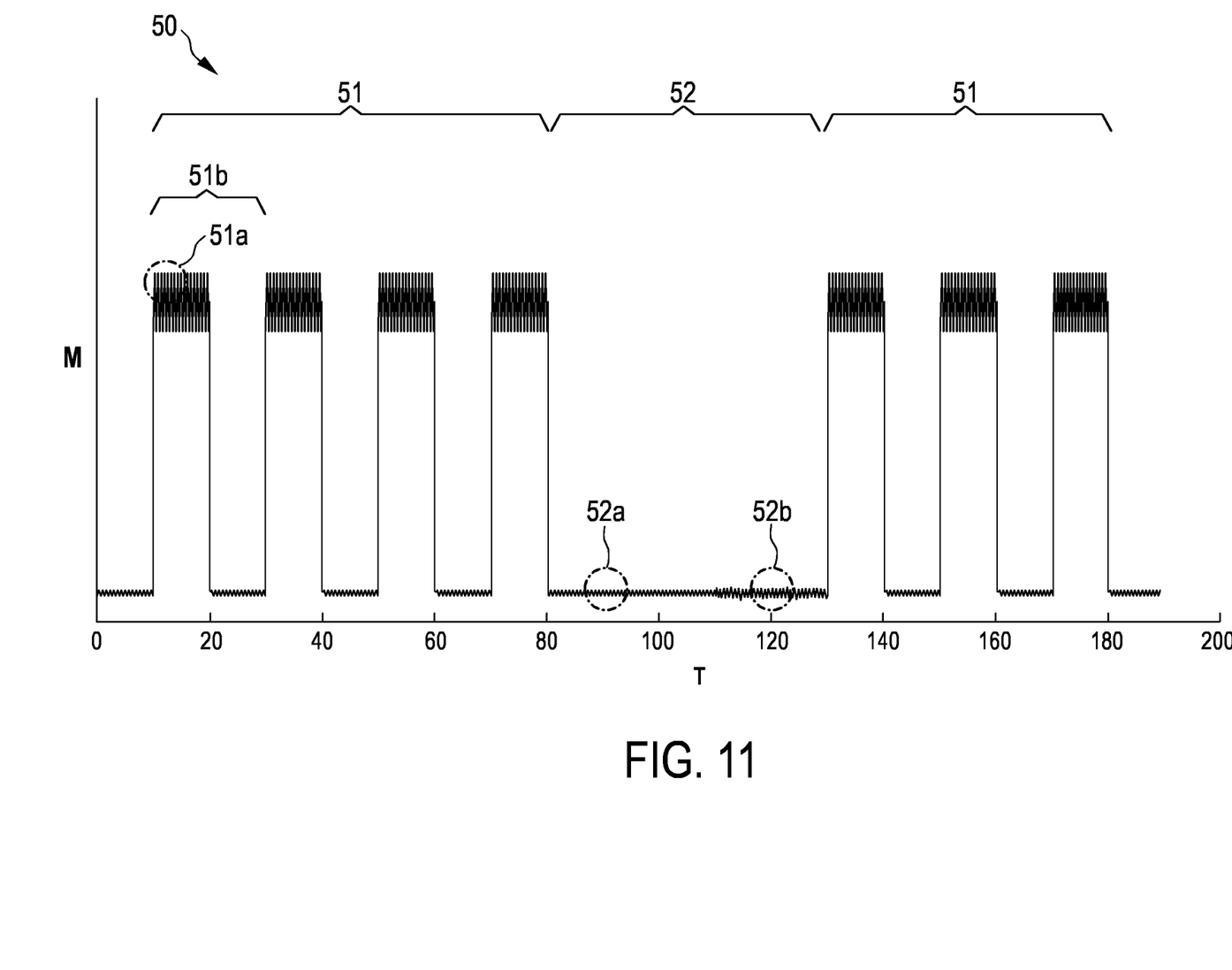
FIG. 11 shows a graph depicting a drinking behavior of a baby.

FIG. 11 shows a graph depicting a drinking behavior of a baby. In FIG. 11, a bottle movement M over time T (sec) is depicted. The drinking behavior 50 includes drinking periods 51 interrupted by non-drinking periods 52. The non-drinking periods 52 can be due to a pausing period 52 or a period 52b during which the baby is playing with the teat. In the drinking period 51, the infant is performing the suck-swallow-breathe sequence 51a. A burst-pause cycle 51b includes a burst period and a pause period. Accordingly, a drinking period 51 comprises several burst-pause-cycles 51b which include a number of suck-swallow-breathe sequences.

Accordingly, with the above described baby bottle device, it is possible to analyze the parameters relating to the suck-swallow-breathe behavior. A drinking burst consists of a plurality of suck-swallow-breathe events. A burst-pause-cycle consists of a number of drinking bursts and a number of pauses in between the drinking bursts.

During a drinking period, the baby performs the required steps to extract milk from the bottle. Such drinking period also includes the short pauses between drinking bursts. The period between two drinking periods is the non-drinking period 52 during which the baby is not performing the steps to extract milk from the bottle. Such non-drinking periods are different from the pauses in a burst-pause cycle 5b as a period is substantially longer than during the pauses in the burst-pause cycle. The non-drinking period 52 can be because of several reasons like pausing 52a of the baby or that the baby is playing with the teat. The detection of the non-drinking period 52 can be performed based on the detected drinking parameters. In particular, the length of drinking interruptions can be compared to a threshold value to determine the drinking period 51 or the non-drinking period 52.

If the baby bottle device has detected a period 52b during which the baby is playing with the teat, the baby bottle device may analyze the movement data in greater detail. Furthermore, the baby bottle device may output a notification that the baby is playing with the teat.

The period 52b during which the baby is playing with the teat can be determined by analyzing the movement signal. This movement signal will have a smaller amplitude than during the burst-pause cycle. Furthermore, the movement signal during the period 52b during which the baby is playing with the teat may have similar properties as during the sucking period.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. A baby bottle device, comprising:
 a fluid container;
 a baby bottle sleeve coupled to the fluid container and comprising at least one movement sensor being configured to detect a movement of the baby bottle device and output movement data;

a movement analyzer configured to analyze a suck-swallow-breathe behavior of a baby based on the movement data from the at least one movement sensor of the baby bottle sleeve, and a communication transmitter configured to electronically transmit the movement data from the at least one movement sensor or the analyzed suck-swallow-breathe behavior from the movement analyzer.

2. The baby bottle device according to claim 1, wherein the baby bottle sleeve is removably attachable to the fluid container.

3. The baby bottle device according to claim 1, wherein the movement analyzer is configured to determine drinking parameters which include at least one of a burst duration, a pause duration, a burst-pause duration ratio, a number of sucks per burst, a sucking frequency, a sucking magnitude and drinking interruptions.

4. The baby bottle device according to claim 1, further comprising:

a post processor configured to perform a post processing of the movement data.

5. The baby bottle device according to claim 4, further comprising:

a teat, wherein the post processor is configured to analyze current drinking parameters to monitor a performance of the teat.

6. The baby bottle device according to claim 1, wherein the movement analyzer is configured to determine drinking periods and non-drinking periods based on the movement data from the at least one movement sensor.

7. A method of analyzing a drinking behavior of a baby using a baby bottle device, which comprises a baby bottle sleeve comprising at least one movement sensor and coupled to the baby bottle device, comprising:

analyzing a suck-swallow-breathe behavior based on detected movement data from the at least one movement sensor of the baby bottle sleeve, and electronically transmitting, via a communication transmitter, the movement data from the at least one movement sensor or the analyzed suck-swallow-breathe behavior.

8. The method of analyzing a drinking behavior of a baby according to claim 7, further comprising:

detecting a movement of the baby bottle device by the at least one movement sensor.

9. The method of analyzing a drinking behavior of a baby according to claim 7, comprising:

determining a burst duration, a pause duration, a burst-pause duration ratio, a number of sucks per burst, a sucking frequency, a sucking magnitude and/or drinking interruptions.

10. A tangible, non-transitory computer-readable medium that stores a computer program for operating a baby bottle device, the computer program comprising program code for causing a baby bottle device to carry out the method of analyzing a drinking behavior of a baby as defined in claim 7, when the computer program is run on a computer controlling the baby bottle device.

11. A baby bottle movement analyzer, comprising:

a movement analyzer configured to analyze a suck-swallow-breathe behavior of a baby based on movement data from a movement sensor of a baby bottle sleeve coupled to a baby bottle, wherein the movement data from the movement sensor of the baby bottle sleeve is electronically transmitted by a communication transmitter, or the analyzed suck-swallow-breathe behavior from the movement analyzer is electronically transmitted by the communication transmitter.

12. The baby bottle movement analyzer according to claim 11, further comprising:

a housing which is configured to be attached to the baby bottle, wherein the movement analyzer is arranged in the housing.

13. The baby bottle movement analyzer according to claim 12, wherein the movement sensor is arranged in the housing.

14. A tangible, non-transitory computer-readable medium that stores a computer program for operating a baby bottle movement analyzer, the computer program comprising program code for causing a baby bottle movement analyzer as defined in claim 11 to analyze a drinking behavior of a baby by analyzing a suck-swallow-breathe behavior of a baby based on movement data from the movement sensor coupled to the baby bottle when the computer program is run on a computer controlling the baby bottle movement analyzer.

* * * * *